(12) United States Patent
Stankovic et al.

(10) Patent No.: US 9,670,288 B2
(45) Date of Patent: Jun. 6, 2017

(54) OSTEOPROTEGERIN IN NEUROPROTECTION

(71) Applicant: Massachusetts Eye and Ear Infirmary, Boston, MA (US)

(72) Inventors: Konstantina Stankovic, Boston, MA (US); Michael McKenna, Southborough, MA (US); Shyan-Yuan Kao, Needham, MA (US); Albert Edge, Brookline, MA (US)

(73) Assignee: Massachusetts Eye and Ear Infirmary, Boston, MA (US)

(*) Notice: Subject to any disclaimer, the term of this patent is extended or adjusted under 35 U.S.C. 154(b) by 0 days.

(21) Appl. No.: 14/218,507

(22) Filed: Mar. 18, 2014

(65) Prior Publication Data
US 2014/0322231 A1    Oct. 30, 2014

Related U.S. Application Data

(63) Continuation of application No. 13/672,535, filed on Nov. 8, 2012, now Pat. No. 8,716,229.

(60) Provisional application No. 61/557,724, filed on Nov. 9, 2011.

(51) Int. Cl.
| | | |
|---|---|---|
| *A61P 27/16* | (2006.01) | |
| *C07K 16/40* | (2006.01) | |
| *A61K 38/17* | (2006.01) | |
| *A61K 31/675* | (2006.01) | |
| *A61K 39/395* | (2006.01) | |
| *A61K 31/352* | (2006.01) | |
| *A61K 31/7105* | (2006.01) | |
| *A61K 31/713* | (2006.01) | |
| *C07K 16/28* | (2006.01) | |

(52) U.S. Cl.
CPC ............ *C07K 16/40* (2013.01); *A61K 31/352* (2013.01); *A61K 31/675* (2013.01); *A61K 31/713* (2013.01); *A61K 31/7105* (2013.01); *A61K 38/1793* (2013.01); *A61K 39/3955* (2013.01); *C07K 16/2878* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,585,997 B2 | 9/2009 | Kashfi | |
| 2003/0008807 A1* | 1/2003 | Levine et al. | 514/1 |

OTHER PUBLICATIONS

Groh et al., Attenuation of MCP-1/CCL2 expression ameliorates neuropathy in a mouse model for Charcot-Marie-Tooth 1X. Human Molecular Genetics, 2010, vol. 19, No. 18 3530-3543.*
Rybak et al., Ototoxicity. Kidney International (2007) 72, 931-935.*
Ohlemiller, Contributions of mouse models to understanding of age- and noise-related hearing loss. Brain Research 1091 (2006) 89-102.*

(Continued)

*Primary Examiner* — Kimberly A Ballard
*Assistant Examiner* — Aurora M Fontainhas
(74) *Attorney, Agent, or Firm* — Fish & Richardson P.C.; Jay Kugler DeYoung; Gina F. Nellesen

(57) ABSTRACT

Methods for treating neurodegeneration, e.g., sensorineural hearing loss, or a demyelinating disease, using bisphosphonates, ERK kinase inhibitors, and osteoprotegerin (OPG) proteins or nucleic acids.

4 Claims, 9 Drawing Sheets

A

B

C

(56) References Cited

OTHER PUBLICATIONS

Boyle et al., Osteoclast differentiation and activation. Nature | vol. 423 | May 15, 2003 | 337-342.*
Kanzaki et al., Bisphosphonate Therapy Ameliorates Hearing Loss in Mice Lacking Osteoprotegerin. Journal of Bone and Mineral Research vol. 24, No. 1, 2009, 43-49. Published online on Aug. 18, 2008.*
Kao et al., Loss of osteoprotegerin expression in the inner ear causes degeneration of the cochlear nerve and sensorineural hearing loss. Neurobiology of Disease 56 (2013) 25-33.*
Brookler et al., "Etidronate for the neurotologic symptoms of otosclerosis: Preliminary study," Ear Nose Throat J., 76:371-376, 379-381 (1997).
Brookler, "Medical treatment of otosclerosis: rationale for use of bisphosphonates," Int. Tinnitus J., 14:92-96 (2008).
Burdon et al., "Signalling, cell cycle and pluripotency in embryonic stem cells," Trends Cell Biol., 12:432-438 (2002).
Carvalho et al., "Anti-inflammatory and anti-nociceptive activity of risedronate in experimental pain models in rats and mice," Clin. Exp. Pharmacol. Physiol., 33:601-606 (2006).
Chen et al., "Dopamine promotes striatal neuronal apoptotic death via ERK signaling cascades," Eur. J. Neurosci., 29:287-306 (2009).
Chen et al., "p38 and ERK, but not JNK, are involved in copper-induced apoptosis in cultured cerebellar granule neurons," Biochem. Biophys. Res. Commun., 379:944-948 (2009).
Chole et al., "Pathophysiology of otosclerosis," Otol. Neurotol., 22:249-257 (2001).
Daroszewska et al., "Mechanisms of disease: genetics of Paget's disease of bone and related disorders," Nat. Clin. Pract. Rheumatol., 2:270-277 (2006).
de Bernardo et al., "Role of extracellular signal-regulated protein kinase in neuronal cell death induced by glutathione depletion in neuron/glia mesencephalic cultures," J. Neurochem., 91:667-682 (2004).
Emery et al., "Osteoprotegerin is a receptor for the cytotoxic ligand TRAIL,"J. Biol. Chem., 273:14363-14367 (1998).
Gates et al., "Presbycusis," Lancet, 366:1111-1120 (2005).
Goicoechea et al., "Alendronate induces antinociception in mice, not related with its effects in bone," Jpn. J. Pharmacol., 79:433-437 (1999).
Hasmim et al., "Zoledronate inhibits endothelial cell adhesion, migration and survival through the suppression of multiple, prenylation-dependent signaling pathways," J. Thromb. Haemost., 5:166-173 (2007).
Henderson and Hamernik, "Biologic Bases of Noise-Induced Hearing Loss," Occup. Med. 10(3):513-534 (1995).
Hequembourg et al., "Spiral ligament pathology: a major aspect of age-related cochlear degeneration in C57BL/6 mice," J. Assoc. Res. Otolaryngol., 2:118-129 (2001).
Jyothi et al., "Unmyelinated auditory type I spiral ganglion neurons in congenic Ly5.1 mice," J. Comp. Neurol., 518:3254-3271 (2010).
Kamiya et al., "Dynamic changes of neuroskeletal proteins in DRGs underlie impaired axonal maturation and progressive axonal degeneration in type 1 diabetes," Exp Diabetes Res., 2009:793281 (2009).
Kanzaki et al., "Bisphosphonate Therapy Ameliorates Hearing Loss in Mice Lacking Osteoprotegerin," Journal of Bone and Mineral Research, 24(1):43-49 (2009—published online on Aug. 18, 2008 at doi: 10.1359/JBMR.080812).
Kanzaki et al., "Bisphosphonate therapy ameliorates hearing loss in mice lacking osteoprotegerin," J. Bone Miner Res., 24:43-49 (2009).
Kao et al., "Osteoprotegerin Signaling During Postnatal Development of the Murine Cochlea: Implications for Survival and Differentiation of Spiral Ganglion Neurons," Association for Research in Otolaryngology, 34th Annual MidWinter Research Meeting, Baltimore, Maryland (Feb. 19-23, 2011) (Abstract 422).
Khosla, "Minireview: the OPG/RANKL/RANK system," Endocrinol., 142:5050-5055 (2001).
Kostenuik et al., "Osteoprotegerin: a physiological and pharmacological inhibitor of bone resorption," Curr. Pharm. Des., 7:613-635 (2001).
Kujawa et al., "Acceleration of age-related hearing loss by early noise exposure: evidence of a misspent youth," J. Neurosci., 26(7):2115-23 (2006).
Kujawa et al., "Adding Insult to Injury: Cochlear Nerve Degeneration after Temporary Noise-Induced Hearing Loss," J. Neurosci., 29:4077-4085 (2009).
Lallemend et al., "Substance P protects spiral ganglion neurons from apoptosis via PKC-Ca2+-MAPK/ERK pathways," J. Neurochem., 87:508-521 (2003).
Lee et al., "Epicatechin protects the auditory organ by attenuating cisplatin-induced ototoxicity through inhibition of ERK," Toxicol. Letters, 199(3):308-316 (2010).
McKenna and Nadol, "Surgery for Otosclerosis," Audio Digest Otolaryngology, 43(16) (Aug. 21, 2010), abstracted summary of Harvard Medical School and Massachusetts Eye and Ear Infirmary Update in Otology and Otologic Surgery, downloaded from http://www.cme-ce-summaries.com/otolaryngology/ot4316.html.
Meltser et al., "Glucocorticoid receptor and mitogen-activated protein kinase activity after restraint stress and acoustic trauma," J. Neurotrauma., 26(10):1835-1845 (2009).
Mizuno et al., "Severe osteoporosis in mice lacking osteoclastogenesis inhibitory factor/osteoprotegerin," Biochem. Biophys. Res. Commun., 247:610-615 (1998).
Monsell, "The mechanism of hearing loss in Paget's disease of bone," Laryngoscope, 114:598-606 (2004).
Previati et al., "Cisplatin cytotoxicity in organ of Corti-derived immortalized cells," J. Cell. Biochem., 101(5):1185-1197 (2007).
Quesnel et al., "Third-generation bisphosphonates for treatment of sensorineural hearing loss in otosclerosis," Otol. Neurotol., 33(8):1308-1314 (2012).
Roelofs et al., "Molecular Mechanisms of Action of Bisphosphonates: Current Status," Clin. Cancer Res., 12:6222s-6230s (2006).
Spoendlin, "Anatomy of cochlear innervation," Am. J. Otolaryngol., 6(6):453-467 (1985).
Starr et al., "The varieties of auditory neuropathy," J. Basic Clin. Physiol. Pharmacol., 11(3):215-230 (2000).
Stazi et al., "Osteoporosis in celiac disease and in endocrine and reproductive disorders," World J. Gastroenterol., 14:498-505 (2008).
Toborek et al., "ERK 1/2 signaling pathway is involved in nicotine-mediated neuroprotection in spinal cord neurons," J. Cell. Biochem., 100:279-292 (2007).
van Campen et al., "Oxidative DNA damage is associated with intense noise exposure in the rat," Hear Res., 64:29-38 (2002).
Walker et al., "Disease modifying and anti-nociceptive effects of the bisphosphonate, zoledronic acid in a model of bone cancer pain," Pain, 100:219-229 (2002).
Wang et al., "Dynamics of noise-induced cellular injury and repair in the mouse cochlea," J. Assoc. Res. Otolaryngol., 3:248-268 (2002).
Whyte et al., "Osteoprotegerin deficiency and juvenile Paget's disease," New Eng. J. Med., 347:175-184, (2002).
Whyte, "Paget's disease of bone and genetic disorders of RANKL/OPG/RANK/NF-kB signaling," Ann. N. Y. Acad. Sci., 1068:143-64 (2006).
Wolfe, "Tau mutations in neurodegenerative diseases," J. Biol. Chem., 284:6021-6025 (2009).
YaŞ il et al., "Further hearing loss during osteoporosis treatment with etidronate," Postgrad Med J., 74:363-364 (1998).
Yasuda et al., "Osteoclast differentiation factor is a ligand for osteoprotegerin/osteoclastogenesisinhibitory factor and is identical to TRANCE/RANKL," Proc. Natl. Acad. Sci. U S A, 95(7):3597-3602 (1998).
Zehnder et al., "Osteoprotegrin knockout mice demonstrate abnormal remodeling of the otic capsule and progressive hearing loss," Laryngoscope, 116(2):201-206 (2006).

(56) References Cited

OTHER PUBLICATIONS

Zehnder et al., "Osteoprotegerin in the inner ear may inhibit bone remodeling in the otic capsule," Laryngoscope, 115(1):172-177 (2005).
Zhou et al., "Role of extracellular signal-regulated kinase in glutamate-stimulated apoptosis of rat retinal ganglion cells," Curr. Eye Res., 32:233-239 (2007).
Zinc et al., "The MAPK/JNK signalling pathway offers potential therapeutic targets for the prevention of acquired deafness," Curr. Drug Targets CNS Neurol Disord., 3(4):325-32 (2004).
Kalinec et al., "A cochlear cell line as an vitro system for drug ototoxicity screening," Audiol Neurootol, 2003;8: 177-189.
Moser et al., "Auditory neuropathy—neural and synaptic mechanisms," Neurology, 12:135-149, 2016.
Parsons et al., "Auditory Fidelity," Nature, 444: 1013-1014, 2006.
Teitelbaum et al., "Bone resorption by osteoclasts," Science, 289: 1504-1508, 2000.
Wei et al., "Interleukin-4 reversibly inhibits osteoclastogenesis via inhibition of NF-KB and Mitogen-activated protein kinase signaling," The Journal of Biological Chemistry, 277:8, 662-6630, 2002.

* cited by examiner

FIGs. 1A-C

SEQUENCE LISTING

<160> NUMBER OF SEQ ID NOS: 2

<210> SEQ ID NO 1
<211> LENGTH: 401
<212> TYPE: PRT
<213> ORGANISM: homo sapiens OPG

<400> SEQUENCE: 1

Met Asn Asn Leu Leu Cys Cys Ala Leu Val Phe Leu Asp Ile Ser Ile
 1               5                  10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro

```
            50                  55                  60
Cys Pro Asp His Tyr Tyr Thr Asp Ser Trp His Thr Ser Asp Glu Cys
 65                  70                  75                  80

Leu Tyr Cys Ser Pro Val Cys Lys Glu Leu Gln Tyr Val Lys Gln Glu
                 85                  90                  95

Cys Asn Arg Thr His Asn Arg Val Cys Glu Cys Lys Glu Gly Arg Tyr
                100                 105                 110

Leu Glu Ile Glu Phe Cys Leu Lys His Arg Ser Cys Pro Pro Gly Phe
            115                 120                 125

Gly Val Val Gln Ala Gly Thr Pro Glu Arg Asn Thr Val Cys Lys Arg
            130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Thr Gln Lys
                165                 170                 175

Gly Asn Ala Thr His Asp Asn Ile Cys Ser Gly Asn Ser Glu Ser Thr
                180                 185                 190

Gln Lys Cys Gly Ile Asp Val Thr Leu Cys Glu Glu Ala Phe Phe Arg
            195                 200                 205

Phe Ala Val Pro Thr Lys Phe Thr Pro Asn Trp Leu Ser Val Leu Val
210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
                260                 265                 270

Asp Ile Asp Leu Cys Glu Asn Ser Val Gln Arg His Ile Gly His Ala
            275                 280                 285

Asn Leu Thr Phe Glu Gln Leu Arg Ser Leu Met Glu Ser Leu Pro Gly
            290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
                340                 345                 350

Lys Thr Tyr His Phe Pro Lys Thr Val Thr Gln Ser Leu Lys Lys Thr
            355                 360                 365

Ile Arg Phe Leu His Ser Phe Thr Met Tyr Lys Leu Tyr Gln Lys Leu
            370                 375                 380

Phe Leu Glu Met Ile Gly Asn Gln Val Gln Ser Val Lys Ile Ser Cys
385                 390                 395                 400

Leu

<210> SEQ ID NO 2
<211> LENGTH: 2354
<212> TYPE: DNA
<213> ORGANISM: homo sapiens OPG

<400> SEQUENCE: 2
tttttttccc ctgctctccc aggggccaga caccaccgcc ccaccsctca cgccccacct      60
ccctggggga tcctttccgc cccagccctg aaagcgttaa ccctggagct ttctgcacac    120
```

```
cccccgaccg ctcccgccca agcttcctaa aaaagaaagg tgcaaagttt ggtccaggat    180
agaaaaatga ctgatcaaag gcaggcgata cttcctgttg ccgggacgct atatataacg    240
tgatgagcgc acgggctgcg gagacgcacc ggagcgctcg cccagccgcc gcctccaagc    300
ccctgaggtt tccggggacc acaatgaaca acttgctgtg ctgcgcgctc gtgtttctgg    360
acatctccat taagtggacc acccaggaaa cgtttcctcc aaagtacctt cattatgacg    420
aagaaacctc tcatcagctg ttgtgtgaca aatgtcctcc tggtacctac ctaaaacaac    480
actgtacagc aaagtggaag accgtgtgcg ccccttgccc tgaccactac tacacagaca    540
gctggcacac cagtgacgag tgtctatact gcagccccgt gtgcaaggag ctgcagtacg    600
tcaagcagga gtgcaatcgc acccacaacc gcgtgtgcga atgcaaggaa gggcgctacc    660
ttgagataga gttctgcttg aaacatagga gctgccctcc tggatttgga gtggtgcaag    720
ctggaacccc agagcgaaat acagtttgca aaagatgtcc agatgggttc ttctcaaatg    780
agacgtcatc taaagcaccc tgtagaaaac acacaaattg cagtgtcttt ggtctcctgc    840
taactcagaa aggaaatgca acacgacaa catatgttc cggaaacagt gaatcaactc    900
aaaaatgtgg aatagatgtt accctgtgtg aggaggcatt cttcaggttt gctgttccta    960
caaagtttac gcctaactgg cttagtgtct tggtagacaa tttgcctggc accaaagtaa    1020
acgcagagag tgtagagagg ataaaacggc aacacagctc acaagaacag actttccagc    1080
tgctgaagtt atggaaacat caaaacaaag accaagatat agtcaagaag atcatccaag    1140
atattgacct ctgtgaaaac agcgtgcagc ggcacattgg acatgctaac ctcaccttcg    1200
agcagcttcg tagcttgatg gaaagcttac cgggaaagaa agtgggagca gaagacattg    1260
aaaaaacaat aaaggcatgc aaacccagtg accagatcct gaagctgctc agtttgtggc    1320
gaataaaaaa tggcgaccaa gacaccttga agggcctaat gcacgcacta aagcactcaa    1380
agacgtacca ctttcccaaa actgtcactc agagtctaaa gaagaccatc aggttccttc    1440
acagcttcac aatgtacaaa ttgtatcaga agttattttt agaaatgata ggtaaccagg    1500
tccaatcagt aaaaataagc tgcttataac tggaaatggc cattgagctg tttcctcaca    1560
attggcgaga tcccatggat gagtaaactg tttctcaggc acttgaggct ttcagtgata    1620
tctttctcat taccagtgac taattttgcc acagggtact aaaagaaact atgatgtgga    1680
gaaaggacta acatctcctc caataaaccc caaatggtta atccaactgt cagatctgga    1740
tcgttatcta ctgactatat tttcccttat tactgcttgc agtaattcaa ctggaaatta    1800
aaaaaaaaaa actagactcc attgtgcctt actaaatatg ggaatgtcta acttaaatag    1860
ctttgagatt tcagctatgc tagaggcttt tattagaaag ccatattttt ttctgtaaaa    1920
gttactaata tatctgtaac actattacag tattgctatt tatattcatt cagatataag    1980
atttgtacat attatcatcc tataaagaaa cggtatgact taattttaga aagaaaatta    2040
tattctgttt attatgacaa atgaaagaga aaatatatat ttttaatgga aagtttgtag    2100
catttttcta ataggtactg ccatattttt ctgtgtggag tattttttata attttatctg    2160 tataagctgt aatatcattt tatagaaaat gcattattta gtcaattgtt taatgttgga    2220
aaacatatga aatataaatt atctgaatat tagatgctct gagaaattga atgtaccta    2280 tttaaaagat tttatggttt tataactata taaatgacat tattaaagtt ttcaaattat    2340
tttttaaaaa aaaa                                                      2354
```

OSTEOPROTEGERIN IN NEUROPROTECTION

CROSS-REFERENCE TO RELATED APPLICATIONS

This application is a continuation of U.S. application Ser. No. 13/672,535, filed Nov. 8, 2012, which claims priority to U.S. Provisional Application Ser. No. 61/557,724, filed on Nov. 9, 2011, which is incorporated by reference in its entirety.

FEDERALLY SPONSORED RESEARCH OR DEVELOPMENT

This invention was made with Government support under Grant No. NIDCD K08 DC010419 awarded by the National Institutes of Health. The Government has certain rights in the invention.

TECHNICAL FIELD

This invention relates to methods for treating neurodegenerative disorders, e.g., sensorineural hearing loss, using bisphosphonates, ERK Kinase inhibitors, and osteoprotegerin (OPG) proteins or nucleic acids.

BACKGROUND

More than 30 million people in the US suffer from hearing loss or vestibular disorders. One in three people older than 60 and one in two people older than 85 have some degree of age-related hearing loss (ARHL). With increased life expectancy, more people from each successive generation will likely suffer from hearing loss. Noise-induced inner ear damage/loss (NIHL) is also a major cause of hearing loss and vestibular disorders, which affects both young and aged populations. The cause of hearing loss, in particular age-related hearing loss (ARHL), is not well understood. As there is presently no effective treatment for hearing loss, hearing loss is a debilitating disorder causing heavy burden for individuals as well as the society.

Mutations in osteoprotegerin (OPG) are linked to juvenile Paget's disease (Whyte, M. P. et al. New Eng J Med. 2002; 347:175-184; Daroszewska A, Ralston S H. Nat Clin Pract Rheumatol. 2006; 2:270-277), an autosomal recessive osteopathy associated with sensorineural or mixed sensorineural and conductive hearing loss. Mechanisms of sensorineural hearing loss in this devastating disease are elusive.

SUMMARY

The present invention is based, at least in part, on the discovery that OPG plays a neuroprotective role, in the ear and in the brain.

Thus, in a first aspect, the invention features methods for treating sensorineural hearing loss not associated with otosclerosis in a subject. The methods include administering to the subject a therapeutically effective amount of a bisphosphonate, an ERK Kinase inhibitor, an osteoprotegerin protein or active fragment thereof or a nucleic acid encoding an osteoprotegerin protein or active fragment thereof. In some embodiments, the hearing loss is selected from the group consisting of age-related hearing loss, noise-induced hearing loss, autoimmune inner ear disease, sudden idiopathic sensorineural hearing loss, Meniere's disease and neurodegenerative hearing loss, as well as sensorineural hearing loss due to genetic mutations, ototoxic drugs (such as aminoglycoside antibiotics, platinum containing chemotherapeutic agents and loop diuretics), infection (including viral, bacterial or fungal), trauma, radiation treatment, tumors (benign and malignant), metabolic derangement (as in diabetes).

In another aspect, the invention provides methods for treating a demyelinating disease in a subject. The methods include the method comprising administering to the subject a therapeutically effective amount of a bisphosphonate, an ERK Kinase inhibitor, an osteoprotegerin protein or active fragment thereof or a nucleic acid encoding an osteoprotegerin protein or active fragment thereof. In some embodiments, the demyelinating disease is selected from the group consisting of multiple sclerosis, neuromyelitis optica, Guillain-Barré syndrome, Charcot-Marie-Tooth disease, peroxisomal disorders, neurofibromatosis type II and sporadic vestibular schwannomas.

In some embodiments, the bisphosphonate is zoledronate.

In some embodiments, the ERK Kinase inhibitor is a small molecule inhibitor, an antibody or antigen-binding fragment thereof that binds to and inhibits ERK kinase, or an inhibitory nucleic acid that targets ERK kinase.

In some embodiments, the osteoprotegerin protein is at least 80% identical to SEQ ID NO: 1.

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient that can be attributed to or associated with treatment by the compositions and methods of the present invention.

The term "subject" is used throughout the specification to describe an animal, human or non-human, to whom treatment according to the methods of the present invention is provided. Veterinary and non-veterinary applications are contemplated. The term includes, but is not limited to, birds and mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the invention will be apparent from the following detailed description and figures, and from the claims.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1. Degenerative changes in the cochlear nerve in OPG deficient mice. (A) A schematic of a cochlear cross section depicting 3 regions that were studied, and sound frequencies that these regions are tuned to. The boxed region in the apex indicates the spiral ganglion that contains somata of cochlear neurons shown in (B) and FIG. 2A. (B) Osmicated, plastic-embedded sections of 10 week old cochlear neurons demonstrate that most WT neurons were individually surrounded by osmiophilic Schwann cells whereas opg –/– neurons formed demyelinated aggregates (*) of degenerating neurons with poorly defined cellular boundaries. (C) The area occupied by degenerating neurons in demyelinated aggregates, when expressed as a fraction of the total neuronal area of a cochlear half turn, was larger and increased faster with age in opg –/– than in WT mice. Data expressed as mean+/–standard error of the mean (SEM); the same convention is used in other figures. N=4-13 ears from 4-10 animals for each age.

DETAILED DESCRIPTION

Figure 2A:
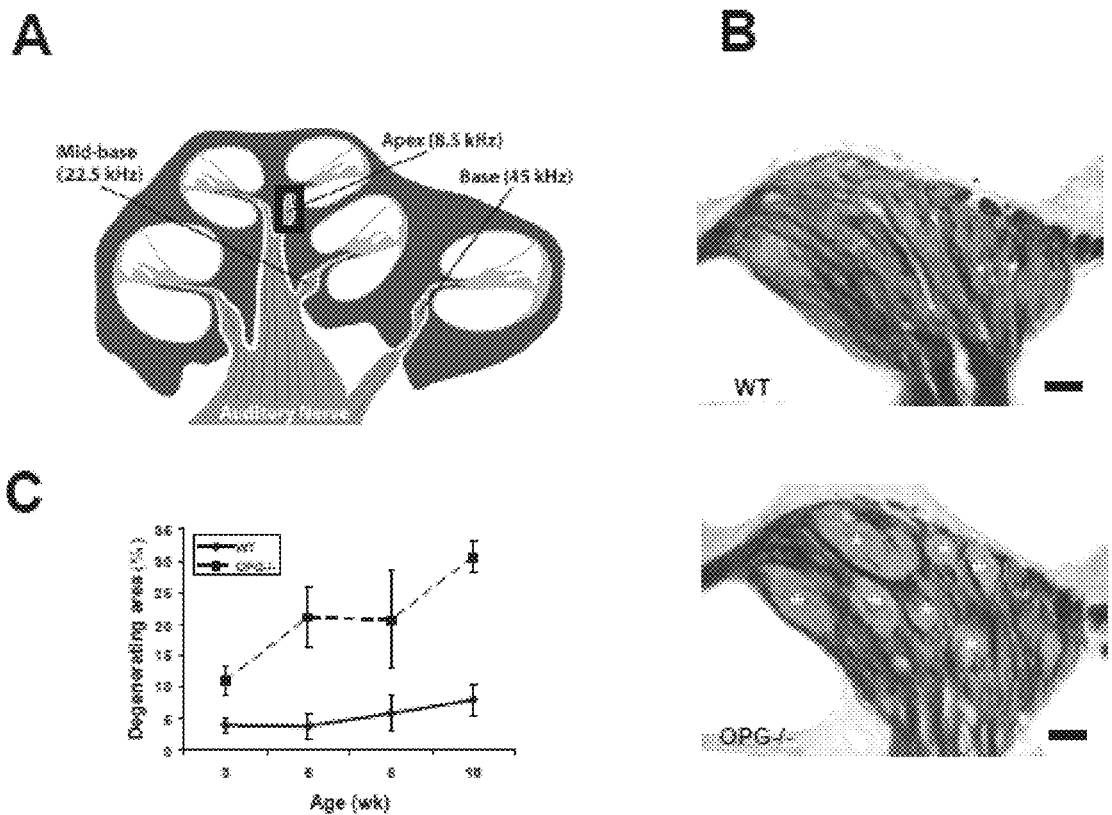
FIG. 2. Demyelination of spiral ganglion neurons in OPG deficient cochlea (A) The fraction of demyelinated neurons in total number of neurons significantly increased with age in opg –/– re age-matched WT mice. (B) The fraction of TuJ expressing (TuJ+) neurons in total number of neurons significantly decreased with age in opg –/– mice. N=6 ears from 3 animals for each age and each group (WT and opg–/–). * signifies P<0.05 by Student's t-test in this and other figures.

As described herein, OPG regulates survival of spiral ganglion cells, and OPG deficiency causes sensorineural hearing loss. These findings provide a new therapeutic strategy for treatment of sensorineural hearing loss by targeting OPG. The present disclosure provides, inter alia, methods and pharmaceutical compositions for treating sensorineural hearing loss and/or vestibular disorders in a subject. More specifically, the present disclosure provides methods and compositions for treating hearing loss in a subject by administering bisphosphonate or ERK Kinase inhibitor, and/or OPG or active fragments thereof, and/or compounds that increases levels of osteoprotegerin (OPG). The finding that OPG is expressed in the brain, as assessed by in situ hybridization, indicated that OPG may be important for survival of different types of neurons in addition to cochlear neurons. Thus, targeting OPG is useful in the treatment of several human diseases.

Osteoprotegerin and Disease

Osteoprotegerin (OPG) is a cytokine receptor, and a member of the tumor necrosis factor (TNF) receptor superfamily. Mutations in OPG are linked to juvenile Paget's disease (Whyte, M. P. et al. New Eng J Med. 2002; 347: 175-184; Daroszewska A, Ralston S H. Nat Clin Pract Rheumatol. 2006; 2:270-277), an autosomal recessive osteopathy associated with sensorineural or mixed sensorineural and conductive hearing loss. Mechanisms of sensorineural hearing loss in this devastating disease are elusive. As described herein, a likely mechanism is degeneration of the Schwann cells and auditory nerve. Additional clinical significance of this study pertains to sensorineural hearing loss associated with osteoporosis, otosclerosis and celiac disease because these diseases are associated with altered OPG levels (Kostenuik P J, Shalhoub V. Curr Pharm Des. 2001; 7:613-635; Stazi A V, Trecca A, Trint, B. World J Gastroenterol. 2008; 14:498-505). Previous mouse studies suggested that deficiency of OPG expression may induce progressive conductive hearing loss (Zehnder A F, Kristiansen A G, Adams J C, Merchant S N, McKenna M J. Laryngoscope. 2005; 115(1):172-177; Zehnder A F, Kristiansen A G, Adams J C, Kujawa S G, Merchant S N, McKenna M J. Laryngoscope. 2006; 116(2):201-206).

ERK Kinase (MEK)

Mitogen-activated protein kinase/extracellular signal-regulated kinase (MAPK/ERK) kinase (MEK) is a key protein kinase in the RAS/RAF/MEK/ERK pathway, which signals for cancer cell proliferation and survival. The present results show that OPG secreted by spiral ganglion cells, which include Schwann cells and neurons, protects these cells from apoptosis induced by oxidative stress or TRAIL by inhibiting ERK. Several studies support the roles of ERK kinase in promoting apoptosis in other neurons induced by free radicals and reactive oxygen species (ROS). First, glutathione depletion in neuron/glia culture induced the generation of ROS thus causing neuronal death through the ROS-dependent activation of ERK signaling pathway (de Bernardo S, Canals S, Casarejos M J, Solano, R M, Menendez J'Mena M A. J Neurochem. 2004; 91:667-682). Second, dopamine promoted apoptotic cell death of striatal neurons through the activation of ERK and cytosolic retention of p-ERK (Chen, J., Rusnak, M., Lombroso, P. J. & Sidhu, A. Eur J Neurosci. 2009; 29:287-306). ROS triggered by copper induced apoptosis in cultured cerebellar granule neurons through the activation of ERK signaling pathway (Chen, X. et al. Biochem Biophys Res Commun. 2009; 379:944-948). These results and others suggested that ERK may be a downstream effector of ROS to induce apoptotic cell death in neurons. However, there are also studies suggesting that activation of ERK kinase suppresses neuronal death. First, nicotine-mediated neuroprotection was partially due to the activation of ERK kinase in spiral cord neurons (Toborek M. et al. J Cell Biochem. 2007; 100:279-292). Second, in rat retinal ganglion cells, the activation of ERK contributed to the suppression of apoptosis induced by glutamate (Zhou R H. et al. Curr Eye Res. 2007; 32:233-239). Third, the activation of ERK pathway was involved in the protection of rat SGNs from apoptosis by substance P (Lallemend F. et al. J Neurochem. 2003; 87:508-521). The published results combined with the present studies suggest that ERK signaling pathway plays an important role in the regulation of survival of auditory neurons under oxidative stress.

OPG and Myelin Degeneration

The present study showed that OPG was expressed in auditory neurons and Schwann cells in inner ear; loss of OPG caused degeneration of Schwann cells and eventually auditory neurons which was consistent with the progressive sensorineural hearing loss observed in OPG−/− mice. Auditory neurons are surrounded by compact myelin (Spoendlin H. Am J Otolaryngol. 1985; 6(6):453-467); loss of myelin in central and peripheral nerves is associated with many human demyelinating diseases such as multiple sclerosis, neuromyelitis optica, Guillain-Barré syndrome, and Charcot-Marie-Tooth disease. Primary demyelination of auditory nerves has been proposed to be an important mechanism of auditory neuropathy (Starr A, Sininger Y S, Pratt H. J Basic Clin Physiol Pharmacol. 2000; 11(3):215-230). The present results suggested that loss of OPG expression results in the loss of myelin sheath and Schwann cells, leading to the degeneration of auditory neurons and finally hearing loss. Since auditory nerve also expresses OPG, loss of OPG may cause primary neuropathy of auditory neurons; as described previously, auditory nerve loss is not noticed for weeks to months and it may take years for auditory neurons to degenerate (Kujawa S G, Liberman M C. J Neurosci. 2009: 29:4077-4085). Nevertheless, without wishing to be bound by theory, the loss of OPG may cause both myelinopathy and neuropathy thus leading to the progressive hearing loss observed in OPG−/− mice; this mechanism may also be applied for hearing loss, e.g., in JPD patients.

Methods of Treatment

The methods described herein include methods for the treatment of disorders associated with neurodegeneration, e.g., sensorineural hearing loss or demyelinating diseases such as multiple sclerosis, neuromyelitis optica, Guillain-Barré syndrome, Charcot-Marie-Tooth disease, peroxisomal disorders, neurofibromatosis type II and sporadic vestibular schwannomas. In some embodiments, the disorder is sensorineural hearing loss that is not associated with otosclerosis, e.g., age-related hearing loss, noise-induced hearing loss, autoimmune inner ear disease, sudden idiopathic sensorineural hearing loss, Meniere's disease or neurodegenerative hearing loss, as well as sensorineural hearing loss due to genetic mutations, ototoxic drugs (such as aminoglycoside antibiotics, platinum containing chemotherapeutic agents, and loop diuretics), infection (including viral, bacterial or fungal), trauma, radiation treatment, tumors (benign and malignant), metabolic derangement (as in diabetes).

Generally, the methods include administering a therapeutically effective amount of a bisphosphonate, OPG (e.g., OPG protein or nucleic acid), or ERK kinase inhibitor to a subject who is in need of, or who has been determined to be in need of, such treatment. Examples of routes of administration include parenteral, e.g., intravenous, intradermal, subcutaneous, oral (e.g., inhalation), transdermal (topical), and transmucosal. In preferred embodiments, the drug is administered directly to the inner ear of the affected subject.

As used in this context, to "treat" means to ameliorate at least one symptom of the disorder associated with neurodegeneration. Where the disorder is sensorineural hearing loss that is not associated with otosclerosis, e.g., as described herein, a treatment will lead to an improvement in hearing. Where the disorder is a neurodegenerative disease associated with demyelination, e.g., as described herein, a treatment will lead to an improvement in one or more clinical symptoms of the disease.

Bisphosphonates

The finding of bisphosphonate zoledronate having an anti-apoptotic effect on SGCs suggests a novel indication for this class of well tolerated drugs: treatment of hearing loss due to degeneration of the auditory nerve. There are anecdotal reports of bisphosphonates ameliorating conductive and/or sensorineural hearing loss in humans (Brookler K. Int Tinnitus J. 2008; 14:92-96).

Bisphosphonates (also called diphosphonates) may have therapeutic effects on other neurodegenerative diseases if OPG signaling proves relevant for other neuronal types.

Previous work has shown that bisphosphonates alleviate pain associated with metastatic bone disease by inhibiting bone resorption (Walker K. et al. Pain. 2002; 100:219-229), and pain not related to bone disease by an intrinsic anti-nociceptive activity (Goicoechea, C, Porras E, Alfaro M J. Jpn J Pharmacol. 1999; 79:433-437; Carvalho A P, Bezerra M M, Girão V C, Cunha F Q, Rocha F A. Clin Exp Pharmacol Physiol. 2006; 33:601-606). The results herein suggest that the basis of the anti-nociceptive activity may be direct modulation of neuronal activity. The effect of zoledronate on Schwann cells was studied because the ERK kinase signaling pathway is a known target of zoledronate in endothelial cells (Hasmim M, Bieler G, Rüegg C. J Thromb Haemost. 2007: 5:166-173). Prevention of conductive hearing loss by a related bisphosphonate, risedronate, was ascribed to its effect on bone resorption, but the present data suggest an alternative explanation. The present experiments suggest a possible novel indication for bisphosphonates: prevention of neural degeneration and the resulting sensorineural hearing loss.

Bisphosphonates have two phosphonate (P03) groups and are similar in structure to pyrophosphate, as shown in structure 1:

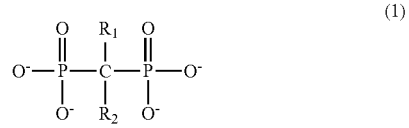
(1)

A number of bisphosphonates are known in the art, including the following:

| Agent | $R_1$ side chain | $R_2$ side chain |
|---|---|---|
| Etidronate | —OH | —$CH_3$ |
| Clodronate | —Cl | —Cl |
| Tiludronate | —H | —S—C6H4—Cl |
| Pamidronate | —OH | —$CH_2$—$CH_2$—$NH_2$ |
| Neridronate | —OH | —$(CH_2)_5$—$NH_2$ |
| Olpadronate | —OH | —$(CH_2)_2N(CH_3)_2$ |
| Alendronate | —OH | —$(CH_2)_3$—$NH_2$ |
| Ibandronate | —OH | —$CH_2$—$CH_2$N($CH_3$)($(CH_2)_4$—$CH_3$) |
| Risedronate | —OH | (pyridinyl-methyl) |
| Zoledronate | —OH | (imidazolyl-methyl) |

A number of bisphosphonates are in current clinical use, including Fosamax (alendronate); Zometa (zoledronic acid); Didronel (etidronate); Reclast (zoledronic acid); Boniva (ibandronate); Actonel (risedronate); Aclasta (zoledronic acid); Aredia (pamidronate); Atelvia (risedronate); and Skelid (tiludronate).

There are two classes of bisphosphonate: N-containing and non-N-containing bisphosphonates. In some embodiments, the present methods include the use of a non-N-containing bisphosphonate.

ERK Kinase Inhibitors

A number of small molecule ERK Kinase inhibitors are known in the art, including CI-1040 and its derivative PD-0325901 (Pfizer; Sebolt-Leopold and Herrera, Nat Rev Cancer 4:937-47 (2004)), MEK162 (ARRY-162) and ARRY-300 (Novartis/Array BioPharma); GDC-0973 (Genentech); AZD6244 ((ARRY-142886; selumetinib; Array Biopharma/AstraZeneca); PD98059 (Cell Signaling #9900; Rundén E et al. J Neurosci. 18(18):7296-305 (1998); Veeranna et al. J Neurosci. 18(11):4008-21 (1998); Xing et al. Mol Cell Biol. 18(4):1946-55 (1998)); U0126 (Duncia et al., Bioorg. Med. Chem. Lett. 8, 2839-44 (1998)); RDEA-119 (BAY-869766) (Ardea Biosciences; Active Biochem Cat. #A-1036); AS703026 (Kim et al., Br J Haematol. 149(4): 537-49 (2010)); AZD8330 (Frémin et al., J Hematol Oncol. 3:8 (2010); TAK-733 (Dong et al. Bioorg Med Chem Lett. 21(5):1315-9 (2011)); PD318088 (Ohren et al., Nat Struct Mol Biol. 11(12):1192-7 (2004); Sebolt-Leopold et al., Nature. 441(7092):457-62 (2006)); GSK1120212 (JTP-74057; Yamaguchi et al., Int J Oncol. 39(1):23-31 (2011); Gilmartin et al., Clin Cancer Res. 17(5):989-1000 (2011)); D-87503 (Maira et al. Biochem Soc Trans. 37(Pt 1):265-72 (2009); BMS 777607 (Dai et al., Mol Cancer Ther. 9(6): 1554-61 (2010); Schroeder et al., J Med Chem. 52(5): 1251-4 (2009)); BIX 02189 (Tatake et al. Biochem Biophys Res Commun. 377(1):120-5 (2008); Obara et al., J Biol Chem. 284(35):23564-73 (2009)); BIX 02188 (Li et al., Biochem Biophys Res Commun. 370(1):159-63 (2008); Obara et al., Mol Pharmacol. 77(1):10-6 (2010)); MSC1936369B (Merck/Serono/Sanofi); VX-702 (Vertex); SL327; Sorafenib (Nexavar, Grupo Espanol, UAlabama, Sanofi, Bayer); GW856553 (GSK); CNI149 (Semapimod, Cytokine PharmaSciences); and SCIO-469 (Scios, Inc). PD-0325901 is an ERK Kinase inhibitor that has been in clinical trials for advanced cancer, see LoRusso et al., Clin Cancer Res 16:1924-1937 (2010); Sebolt-Leopold et al. Proc Amer Assoc Cancer Res. 45 (2004). See also Messersmith et al., Clinical Advances in Hematology & Oncology 4(11):831-836 (2006).

Antibodies or antigen binding fragments thereof (e.g., Fab or F(ab')$_2$) that bind to and inhibit ERK kinase (MEK) can also be used, e.g., antibodies commercially available from Abcam; AbD Serotec; AbFrontier Co., Ltd.; Abgent; Abnova Corporation; ABR, now sold as Thermo Scientific Pierce Antibodies; Acris Antibodies GmbH; AnaSpec; antibodies-online; antibodies-online GmbH; Assay Biotech; Assay Designs/Stressgen (Now Enzo Life Sciences); Atlas Antibodies; Aviva Systems Biology; BD Biosciences; Bethyl Laboratories; BioLegend; Biorbyt; Bioss Corporation; Bioss Inc.; BioVision; Bioworld Technology; Cayman Chemical; CEDARLANE Laboratories Limited; Cell Sciences; Cell Signaling Technology; Covance, Inc.; ECM Biosciences; EMD Millipore; EMD Millipore; Enzo Life Sciences, Inc.; Epitomics, Inc.; EXBIO Praha, a.s.; Fitzgerald Industries International; GeneTex; GenWay Biotech, Inc.; IMGENEX; Invitrogen; Invitrogen; LifeSpan BioSciences; MBL International; MyBioSource.com; Novus Biologicals; OriGene Technologies; ProSci, Inc; Proteintech Group, Inc.; R&D Systems; Raybiotech, Inc.; Rockland Immunochemicals, Inc.; Santa Cruz Biotechnology, Inc.; Sigma-Aldrich; SignalChem; Signalway Antibody Co., Ltd; Spring Bioscience; and Thermo Scientific Pierce Protein Research Products.

Alternatively, inhibitory nucleic acids directed against MEK can be used, e.g., inhibitory nucleic acids that are complementary to the human MEK sequence (i.e., the sequence available in GenBank at Acc. No. NM_005921.1), such as antisense oligonucleotides, small interfering RNAs, including but not limited to an shRNA or siRNA, or antagomirs. A number of algorithms are known in the art for designing inhibitory nucleic acids, and "gene walk" methods as known in the art can be used to optimize the inhibitory activity of the nucleic acids. The nucleic acids can include modifications, e.g., to enhance delivery, half-life, or affinity, including the presence of one or more cholesterol moieties, e.g., at the 3'-end; a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326. In general the inhibitory nucleic acids will be synthesized using methods known in the art.

Osteoprotegerin Protein and Nucleic Acid

Osteoprotegerin, also known as osteoclastogenesis inhibitory factor (OCIF), or tumor necrosis factor receptor superfamily member 11B (TNFRSF11B), MGC29565, OCIF, TR1, and OTTHUMP00000228056, is encoded in humans by the TNFRSF11B gene (Simonet et al., Cell 89 (2): 309-19 (1997). The protein sequence of human OPG can be found at GenBank Ref. No. NP_002537.3; the human OPG nucleic acid sequence is available at GenBank Ref. No. NM_002546.3.

```
Human OPG protein sequence (SEQ ID NO: 1):
MNNLLCCALVFLDISIKWTTQETFPPKYLHYDEETSHQLLCDKCPPG

TYLKQHCTAKWKTVCAPCPDHYYTDSWHTSDECLYCSPVCKELQYVK

QECNRTHNRVCECKEGRYLEIEFCLKHRSCPPGFGVVQAGTPERNTV

CKRCPDGFFSNETSSKAPCRKHTNCSVFGLLLTQKGNATHDNICSGN

SESTQKCGIDVTLCEEAFFRFAVPTKFTPNWLSVLVDNLPGTKVNAE

SVERIKRQHSSQEQTFQLLKLWKHQNKDQDIVKKIIQDIDLCENSVQ

RHIGHANLTFEQLRSLMESLPGKKVGAEDIEKTIKACKPSDQILKLL

SLWRIKNGDQDTLKGLMHALKHSKTYHFPKTVTQSLKKTIRFLHSFT

MYKLYQKLFLEMIGNQVQSVKISCL

Human OPG nucleic acid sequence (SEQ ID NO: 2):
   1 ttttttccc ctgctctccc aggggccaga caccaccgcc
     ccaccctca cgccccacct 61 ccctggggga tcctttccgc cccagccctg aaagcgttaa
     ccctggagct ttctgcacac 121 ccccgaccg ctcccgccca agcttcctaa aaagaaagg
     tgcaaagttt ggtccaggat 181 agaaaaatga ctgatcaaag gcaggcgata cttcctgttg
     ccgggacgct atatataacg 241 tgatgagcgc acgggctgcg gagacgcacc ggagcgctcg
     cccagccgcc gcctccaagc 301 ccctgaggtt tccggggacc acaatgaaca acttgctgtg
     ctgcgcgctc gtgtttctgg 361 acatctccat taagtggacc acccaggaaa cgtttcctcc
     aaagtacctt cattatgacg 421 aagaaacctc tcatcagctg ttgtgtgaca aatgtcctcc
     tggtacctac ctaaaacaac 481 actgtacagc aaagtggaag accgtgtgcg ccccttgccc
     tgaccactac tacacagaca 541 gctggcacac cagtgacgag tgtctatact gcagcccgt
     gtgcaaggag ctgcagtacg 601 tcaagcagga gtgcaatcgc acccacaacc gcgtgtgcga
     atgcaaggaa gggcgctacc 661 ttgagataga gttctgcttg aaacatagga gctgccctcc
     tggatttgga gtggtgcaag 721 ctggaacccc agagcgaaat acagtttgca aaagatgtcc
     agatgggttc ttctcaaatg 781 agacgtcatc taaagcaccc tgtagaaaac acacaaattg
     cagtgtcttt ggtctcctgc 841 taactcagaa aggaaatgca acacgaca acatatgttc
     cggaaacagt gaatcaactc 901 aaaaatgtgg aatagatgtt accctgtgtg aggaggcatt
     cttcaggttt gctgttccta 961 caaagtttac gcctaactgg cttagtgtct tggtagacaa
     tttgcctggc accaaagtaa 1021 acgcagagag tgtagagagg ataaaacggc aacacagctc
     acaagaacag actttccagc 1081 tgctgaagtt atggaaacat caaaacaaag accaagatat
     agtcaagaag atcatccaag 1141 atattgacct ctgtgaaaac agcgtgcagc ggcacattgg
     acatgctaac ctcaccttcg 1201 agcagcttcg tagcttgatg gaaagcttac cgggaaagaa
     agtgggagca gaagacattg 1261 aaaaaacaat aaaggcatgc aaacccagtg accagatcct
     gaagctgctc agtttgtggc 1321 gaataaaaaa tggcgaccaa gacaccttga agggcctaat
     gcacgcacta aagcactcaa 1381 agacgtacca ctttcccaaa actgtcactc agagtctaaa
     gaagaccatc aggttccttc 1441 acagcttcac aatgtacaaa ttgtatcaga agttattttt
     agaaatgata ggtaaccagg 1501 tccaatcagt aaaaataagc tgcttataac tggaaatggc
     cattgagctg tttcctcaca 1561 attggcgaga tcccatggat gagtaaactg tttctcaggc
     acttgaggct ttcagtgata 1621 tctttctcat taccagtgac taattttgcc acagggtact
     aaaagaaact atgatgtgga 1681 gaaggacta acatctcctc caataaaccc caaatggtta
     atccaactgt cagatctgga 1741 tcgttatcta ctgactatat tttcccttat tactgcttgc
     agtaattcaa ctggaaatta
```

-continued

```
1801  aaaaaaaaaa actagactcc attgtgcctt actaaatatg
      ggaatgtcta acttaaatag 1861  ctttgagatt tcagctatgc tagaggcttt tattagaaag
      ccatattttt ttctgtaaaa 1921  gttactaata tatctgtaac actattacag tattgctatt
      tatattcatt cagatataag 1981  atttgtacat attatcatcc tataaagaaa cggtatgact
      taattttaga aagaaaatta 2041  tattctgttt attatgacaa atgaaagaga aaatatatat
      ttttaatgga aagtttgtag 2101  catttttcta ataggtactg ccatattttt ctgtgtggag
      tattttata attttatctg 2161  tataagctgt aatatcattt tatagaaaat gcattattta
      gtcaattgtt taatgttgga 2221  aaacatatga aatataaatt atctgaatat tagatgctct
      gagaaattga atgtacctta 2281  tttaaaagat tttatggttt tataactata taaatgacat
      tattaaagtt ttcaaattat 2341  tttttaaaaa aaaa
```

OPG has also been described in other species, including *Mus musculus* (NM_008764.3 (nucleic acid) and NP_032790.3 (protein)) and *Rattus Norvegicus* (NM_012870.2 (nucleic acid) and NP_037002.1 (protein)). In the present methods, it will generally be desirable to use an OPG that is from the same species as the subject to be treated.

The method described herein can include the administration of OPG protein or nucleic acid, or active fragments thereof that retain the ability to suppress apoptosis in opg$^{-/-}$ spheres. In some embodiments, the active fragments comprise 1, 2, 3, or all 4 of the TNFR-Cysteine rich regions present in the wild type protein (at aa 24-62; 65-105; 107-142; and 145-185), and one or both of the Death (aa 281-364) and Death-Like (aa 231-272) Domains. In some embodiments, the OPG protein is at least 80% identical to SEQ ID NO:1, e.g., at least 85%, 90%, 95%, or 99% identical to SEQ ID NO:1. In some embodiments, the OPG nucleic acid is at least 80% identical to SEQ ID NO:2, e.g., at least 85%, 90%, 95%, or 99% identical to SEQ ID NO:2, or encodes a protein that is at least is at least 80% identical to SEQ ID NO:1, e.g., at least 85%, 90%, 95%, or 99% identical to SEQ ID NO:1.

The comparison of sequences and determination of percent identity between two sequences can be accomplished using a mathematical algorithm. For example, the percent identity between two amino acid sequences can determined using the Needleman and Wunsch ((1970) J. Mol. Biol. 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

The methods described herein can include administering nucleic acids encoding an OPG polypeptide or active fragment thereof, or a nucleic acid encoding a protein that increases OPG expression, level or activity, can be incorporated into a gene construct to be used as a part of a gene therapy protocol. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct into the inner ear.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In addition to viral transfer methods, such as those illustrated above, non-viral methods can also be employed to cause expression of a nucleic acid compound described herein (e.g., an OPG nucleic acid or a nucleic acid encoding OPG or a compound that increases OPG expression, levels or activity) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21): 1867-74 (2000).

In some embodiments, a gene encoding OPG is entrapped in liposomes, e.g., bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Pharmaceutical Compositions and Methods of Administration

The methods described herein include the manufacture and use of pharmaceutical compositions, which include OPG as an active ingredient. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Dosage

The terms "effective amount" and "effective to treat," as used herein, refer to an amount or a concentration of one or more compounds or a pharmaceutical composition described herein utilized for a period of time (including acute or chronic administration and periodic or continuous administration) that is effective for treating or preventing hearing loss.

Effective amounts of one or more compounds or a pharmaceutical composition for use in the present invention include amounts that treat sensorineural hearing loss, e.g., prevent or delay the onset, delay or halt the progression, ameliorate the effects of, or generally improve the prognosis of a subject diagnosed with sensorineural hearing loss, e.g., one or more of the diseases described herein. For example, in the treatment of hearing impairment, a compound that improves hearing to any degree or delays or arrests any symptom of hearing impairment would be therapeutically effective. A therapeutically effective amount of a compound is not required to cure a disease but will provide a treatment for a disease.

An "effective amount" can be the same or different from a prophylactically effective amount, which is an amount necessary to prevent onset of disease or disease symptoms.

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Example 1

Osteoprotegerin Secreted by the Inner Ear Promotes Survival of Cochlear Schwann Cells, Neurons and Stem Cells The following materials and methods were used in the experiments described in this Example.

Reagents and Antibodies

Antibodies (anti-ERK, anti-p-ERK, anti-JNK, anti-p-JNK, anti-p38, anti-p-p38, anti-NF-κB p65, anti-p-NF-κB p65, anti-β actin and anti-cleaved caspase 3) were obtained from Cell Signaling. Anti-BrdU antibody was obtained from Sigma, anti-TuJ antibody from Covance and anti-MBP from Novus Biologicals. OPG and RANKL were from R & D Systems. PD 98059 was from Sigma-Aldrich. Zoledronate was from Novartis.

Mice Strain

Homozygous opg −/− mice were obtained from CLEA-Japan, Inc. They were generated by disruption of exon 2 in the opg locus and backcrossing to the parental C57BL/J6 strain (Mizuno A, et al. Biochem Biophys Res Commun. 1998; 247:610-615). Wild type C57BL/6J mice were obtained from Jackson Laboratory (Bar Harbor, Me.). All animal procedures were approved by the Animal Care and Use Committee of the Massachusetts Eye and Ear Infirmary.

Plastic Embedding for Histopathological Examination

Animals were intracardially perfused with 2.5% glutaraldehyde/1.5% paraformaldehyde in 0.1M phosphate buffer (PB). Animals of the following ages were studied: 3 wk, 6 wk, 8 wk and 10 wk. N=4-13 ears from 4-10 animals per age. Cochleae were extracted, the round window membrane was pierced and flushed with fixative to ensure perfusion of the entire cochlea, and the cochleae were post-fixed overnight. Cochleae were incubated in 1% osmium tetroxide for 60 min, rinsed with ddH$_2$O before decalcification in 0.12M EDTA in 0.1 M PB with 1% glutaraldehyde (pH 7) for 3-4 days on a shaker at room temperature. The samples were dehydrated with 70%, 95% and 100% ethanol and incubated with propylene oxide (PO) for 30 min. Cochleae were embedded in araldite-PO (1:1) for 1 hr followed by araldite-PO (2:1) overnight, degassed in vacuum for 2 hr, and placed in a 60° C. oven for at least 2 days. Cochleae were cut into 20 μm midmodiolar sections and examined under a microscope using Normarski DIC optics.

Paraffin Embedding for In Situ Hybridization and Immunohistochemistry

Animals were intracardially perfused with 4% paraformaldehyde in 0.1M phosphate buffer (PB). Animals of the following ages were studied: 6 wk, 10 wk and 16 wk. N=6 ears from 3 animals per age. In situ hybridization for opg was performed on 10 μm thick paraffin-embedded cochlear sections as previously described (Stankovic K M, Adachi O, Tsuji K, Kristiansen A G, Adams J C, Rosen V, McKenna M J. Hear Res. 2010; 265: 83-89) using the anti sense probe from nucleotide 133 to 668 of opg mRNA (Heinrich J, Bsoul S, Barnes J, Woodruff K, Abboud S. Arch Oral Biol. 2005; 50(10):897-908). The sense probe served as a control, and gave no signal.

Immunohistochemistry was performed using anti-TuJ or anti-MBP primary antibodies, and 568 Alexa Fluor anti-rat or anti-mouse secondary antibodies. For combined in situ hybridization and immunohistochemistry, in situ hybridization was performed first, as described above and using a TSA PLUS Fluorescence Kit (PerkinElmer) according to the manufacture's instructions, followed by immunohistochemistry.

Spiral Ganglion Cell Culture

Cochleae were retrieved from postnatal day 6-7 mice and placed in ice-cold Hank's balanced salt solution (HBSS, Invitrogen). The modiolus was isolated from the surrounding tissue, cut into ~3 pieces, and transferred to an enzymatic solution containing trypsin (2.5 mg/ml) at 37° C. for 20 min. The enzymatic digestion was terminated by replacing the supernatant with culture medium. The tissue was dissociated by gentle mechanical trituration with a pipette. The cell suspension was sequentially plated onto dry non-coated 35 ml dishes. The final plating was transferred into poly-L-ornithine coated cell culture plates. Cultures were maintained in a humidified 5% CO$_2$ incubator at 37° C. The culture medium contained Dulbecco's modified eagle's medium (DMEM) and F-12 (1:1 v:v), 10% FBS, 5% horse serum, NT-3 (20 ng/ml), BDNF (5 ng/ml), 2% B-27 supplement, penicillin (100 U/ml), and streptomycin (100 µg/ml). Some cultures were pre-treated for 3 hours and then co-treated with OPG (100 ng/l), PD98059 (20 nM) or zoledronate (10 µM) 24 hr prior to treatment with 500 µM $H_2O_2$ or TRAIL (100 ng/ml). To eliminate neurons, cultures were treated with 1 µM β-bungarotoxin for 3 days then changed to 0.5 µm for 3 more days. To selectively culture fibroblasts as a control, cells that attached to the culture dish after the first plating were cultured in DMEM supplemented with 10% FBS.

OPG ELISA

SGCs were grown in culture plates. After 24 hours, the culture medium was collected and the cell debris was cleared by spinning at 14,000 g for 10 min at 4° C. Quantification of the OPG levels in the culture media was performed according to the manufacturer's manual (Mouse Quantikine OPG/TNFSRSF11b Immunoassay, R&D Systems).

Cellular Viability Assay and Neuronal Staining

For nuclear condensation assays, cells were cultured on glass cover slips in 24-well plates. After treatment with DNA damaging agents, cells were washed three times with PBS and fixed with 4% paraformaldehyde. Apoptotic cells were detected by staining with 1 µg/ml Hoechst 33342 (Sigma) for 5 min and observed by fluorescence microscopy (Zeiss).

For cleaved caspase 3 immunohistochemistry, cochlear sections were incubated with an anti-cleaved caspase 3 antibody (Cell Signaling, rabbit) overnight. After 3 washing steps with PBST, anti-rabbit secondary antibodies conjugated to Alexa Fluor (rb) 555 were used to detect primary antibodies. Staining was visualized with epifluorescence microscopy (Axioskop 2 Mot Axiocam, Zeiss).

Immunoblotting

Cultured cochlear SGCs were collected and lysed in RIPA-DOC buffer (50 mM Tris buffer (pH 7.2), 150 mM NaCl, 1% Triton-X100, 1% deoxycholate and 0.1% SDS) with protease inhibitors (Complete, Roche, Indianapolis, Ind.). An equal amount of protein extract was loaded per lane, resolved by 4-20% SDS-PAGE, and electro-transferred onto a PVDF membrane (Immobilon-P, Millipore). Protein bands were probed with different primary antibodies and immunoreactivity was detected with an enhanced chemiluminescence detection kit (ECL, Amersham Pharmacia Biotech). The expression of α-actin was used as an internal loading control.

Real-Time Quantitative RT-PCR

Total RNA was purified from cultured cochlear SGCs using RNeasy spin-columns (Qiagen) according to the manufacturers' protocol and a modification for hypocellular, dense connective tissues (Reno C, Marchuk L, Sciore P, Frank C B, Hart D A. 1997. Biotechniques. 1997; 22:1082-1086). Total RNA was reverse transcribed with Taqman Reverse Transcription Reagents kit (Applied Biosystems). Real-time quantitative RT-PCR was performed using 6-FAM linked fluorescent probes and primers designed and optimized by Applied Biosystems. The measurements were carried out on the Mx3005P (Stratagene) using 96-well plates. For each well, the 25 µl reaction contained: 1.25 µl of the 20× probe/primer mix, 1 µl of cDNA template, 12.5 µl Universal Master Mix (Applied Biosystems), and 10.25 µl distilled water. For each gene, there were 3 technical and 4 biological replicates. Fluorescence data were collected over 45 cycles of PCR that consisted of an initial denaturation step at 95° C. for 10 min, followed by 45 cycles of 95° C. for 15 s and 60° C. for 1 min. Gene expression levels were quantified relative to the 18S rRNA gene, and compared between bone types using the Comparative threshold cycle ($C_T$) method, i.e. the $\Delta\Delta C_T$ method (Livak K J, Schmittgen T D. Method Methods. 2001; 25:402-408).

Culture and Analysis of Neurospheres

For each experiment, spiral ganglia of four to six 1-3 day old WT or opg –/– mice were dissected in HBSS. The SGCs (neurons and glia) were dissociated using trypsin (0.25%) for 13 min in PBS at 37° C. The enzymatic digestion was stopped by adding 10% FBS in DMEM-high glucose medium. The tissue was washed twice and gently triturated. The cell suspension was passed through a 70 µm cell strainer (BD Labware). Single cells were cultured in DMEM-high glucose and F12 (mixed 1:1) supplemented with N2 and B27 (Invitrogen), EGF (20 ng/mL; Chemicon), bFGF (10 ng/mL; Chemicon), IGF-1 (50 ng/mL; Chemicon), and heparan sulfate (50 ng/mL; Sigma). Newly formed spheres were cultured in ultra-low-cluster plates (Costar) for 4 days and were termed first generation spheres. Spheres were subsequently passaged every 4 days until the third generation, when 5-10 spheres were collected and dissociated (Oshima K, Grimm C M, Corrales C E, Senn P, Martinez Monedero R, Géléoc GS, Edge A, Holt J R, Heller S. 2007. J Assoc Res Otolaryngol. 2007; 8:18-31). Spheres were passaged at a clonal level for 3 more times. Before each passage, the sphere morphology was assessed and the spheres were counted using the Metamorph counting software. At the third generation, spiral ganglion spheres from WT and opg –/– mice were separated into 4 groups and treated with Rankl (100 ng/ml), OPG (100 ng/ml) or zoledronate (1 µM). The control group was untreated. After 3 days of treatment, the spheres were passaged and treated again for 3 days. Twelve hours before plating, proliferating cells in the spheres were labeled with BrdU (3 µg/ml). After 12 hours, the spheres were plated for 1 hour on poly-L-lysine (0.01%, Cultrex)-coated glass coverslips (Marienfeld GmbH, Germany), fixed in 4% paraformaldehyde for 10 min, treated with 1N HCl for antigen retrieval for BrdU staining, incubated for 1 hour in blocking solution (0.3% Triton, 15% goat serum in 1×PBS), and incubated overnight with either anti-cleaved caspase3 antibody to assess cell death, or anti-BrdU antibody to assess cell proliferation. After 3 washing steps with 1×PBS, the spheres were incubated in secondary antibody for 2 hours (568 Alexa Fluor anti rat or anti mouse). Nuclei were stained with DAPI. Staining was visualized by epifluorescence microscopy (Axioskop 2 Mot Axiocam, Zeiss). Counting was done with the Metamorph software.

Statistical Analysis

Student's t test was used to compare the data presented in all figures. Differences were considered significant if $P<0.05$.

The following describes the results of the experiments.

Cochlear Nerve Degenerates in OPG-Deficient Mice

To gain insight into mechanisms of hearing loss in JPD, cochlear pathology was studied in opg –/– mice (Mizuno A, et al. Biochem Biophys Res Commun. 1998; 247:610-615), a model for JPD. Cochlear sections from wild type (WT) and opg –/– mice were studied first to investigate whether loss of OPG expression caused any inner ear pathology. Osmium stained sections of 3- to 16-wk old inner ears from opg –/– and WT mice were examined by light microscopy. The first pathologic sign in opg –/– mice was demyelination and clustering of cochlear neurons into aggregates with poorly defined cellular boundaries (FIG. 1A, B). Similar pathology has been described with aging (13) and in Ly5.1 mice (Jyothi V, Li M, Kilpatrick L A, Smythe N, LaRue A C, Zhou D, Schulte B A, Schmiedt R A, Lang H. J Comp Neurol. 2010; 518:3254-3271). The degenerative changes were first notable in the cochlear apex and were characterized by patchy areas of pale looking neuronal somata with markedly reduced 3D definition when using differential interference contrast microscopy (FIG. 1B). The area involving these degenerating neuronal somata were expressed as a fraction of the total neuronal area of a cochlear half turn, increased substantially from 3-10 weeks (FIG. 1C). The opg −/− neurons also showed swelling of the space between the cell body and the enwrapping Schwann cell, as reported in mice cochlea after noise trauma (Wang Y, Hirose K, Liberman M C. J Assoc Res Otolaryngol. 2002; 3:248-268).

Demyelination of spiral ganglion neurons in OPG-deficient mice

Figure 2B:
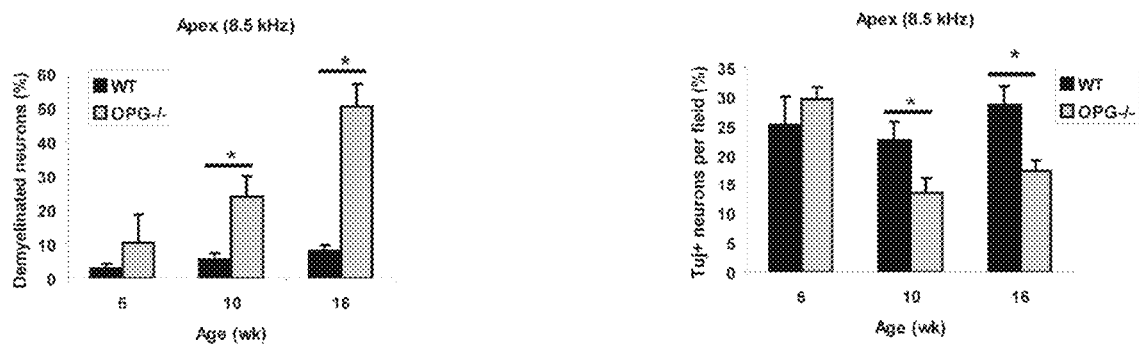
Figure 8A:
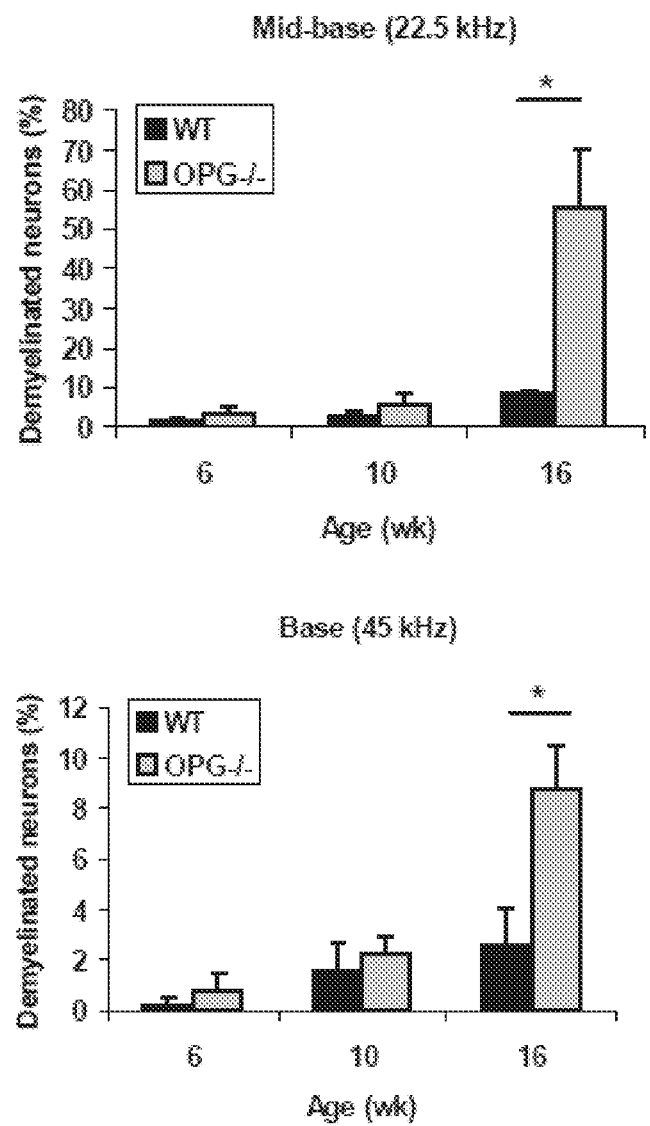
FIG. 8. Neuronal demyelination (A) and the number of TuJ expressing neurons (B) in opg –/– re WT mice progressed in a spatial gradient from the cochlear apex to the base. Demyelination became statistically significant at 10 weeks of age in the apex (FIG. 2B), and at 16 weeks of age in the mid base and base (A). A statistically significant decrease in the fraction of TuJ+neurons was first detected at 10 weeks of age in the apex (FIG. 2C); the difference did not reach statistical significance in the mid base and base by 16 weeks of age.
Figure 8B:
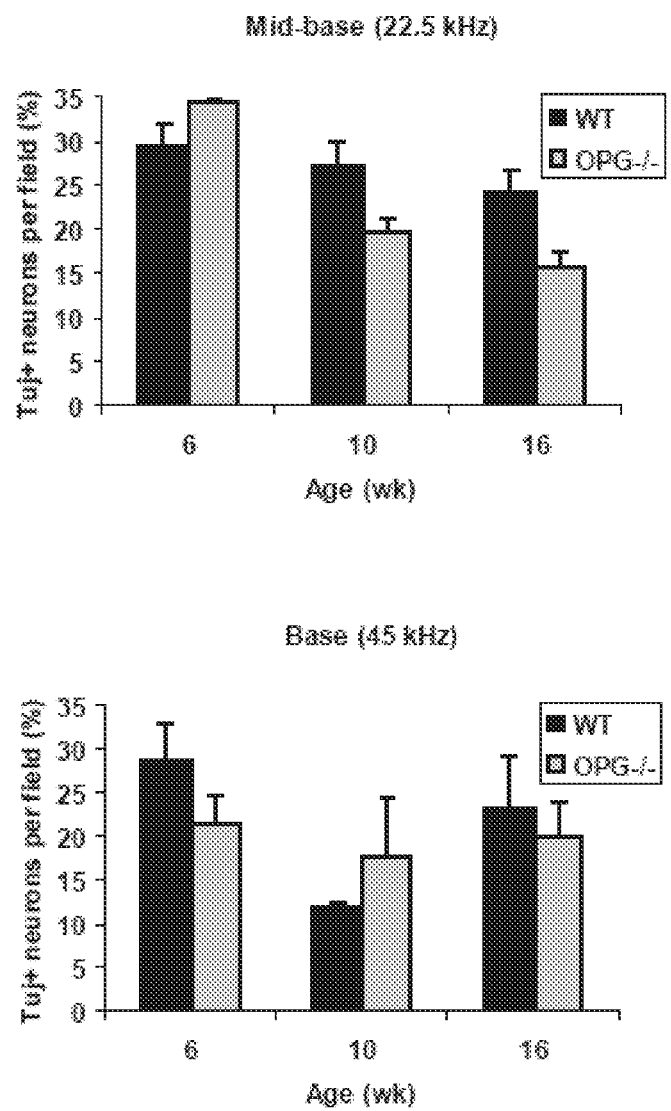

To investigate the temporal correlation between demyelination and neuronal degeneration, immunohistochemistry was performed with antibodies against β-III tubulin (TuJ), or Schwann cell specific myelin basic protein (MBP) on cochlear sections from WT and opg −/− mice at 6, 10, and 16 wks. Stained cells were counted in 3 cochlear regions schematized in FIG. 1A. The number of demyelinated neurons in opg−/− cochleae significantly increased by 10 wks in the cochlear apex (FIG. 2A), and progressed to involve the mid base and base by 16 wks (FIG. 8A). Cochlear neurons began to lose TuJ expression in parallel (FIG. 2B and FIG. 8B), which was consistent with neural degeneration (Kamiya H, Zhang W, Sima A A. Exp Diabetes Res. 2009; 2009:793281; Wolfe M S. J Biol Chem. 2009; 284:6021-6025) even in the absence of neuronal loss, nuclear fragmentation or cleaved caspase 3 expression. These results suggest that OPG deficiency leads to premature aging, and that demyelination precedes neural degeneration and Schwann cell loss.

Cochlear Neurons and Schwann Cells Express and Secrete OPG

Figure 3A:
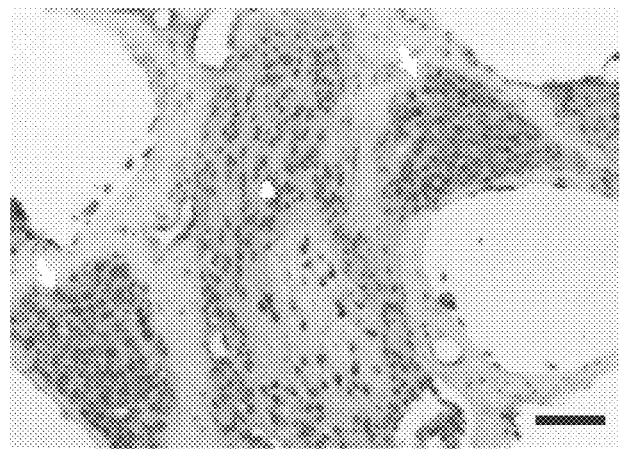
FIG. 3. Expression and secretion of OPG by cochlear neurons and Schwann cells. (A) In situ hybridization for opg demonstrates strong signal in cochlear neurons (white arrow) and Schwann cells (white arrowhead). Scale bar: 100 µm. (B) Measurements of secreted OPG in culture medium of spiral ganglion cells and fibroblasts. OPG is abundantly secreted by WT spiral ganglion cells (SGCs) but not secreted by opg –/– cells (N=3); ND: not detectable. (C) Treatment of cultured SGCs with $H_2O_2$ resulted in more nuclear condensations in opg –/– cells than in WT cells, as shown in representative images (left), and quantified with a bar graph (right); N=4. The nuclei were stained with Hoechst 33342, a fluorescent DNA-binding dye, 24 hours after $H_2O_2$ treatment.
Figure 3B:
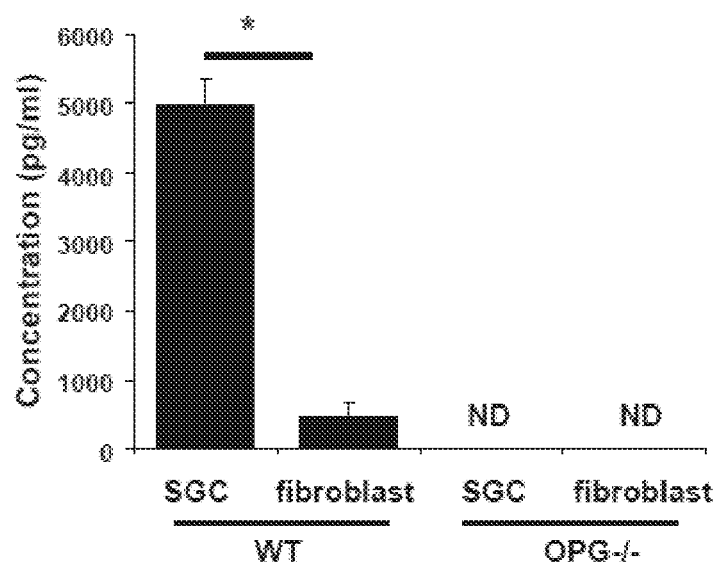

Because the first sign of pathology in opg −/− cochleas is demyelination of cochlear neurons, the next experiments focused on cochlear Schwann cells to investigate the mechanisms in vitro. Cultured cells extracted from the cochlear modiolus, and termed spiral ganglion cells (SGCs), consisted of >90% Schwann cells and ~10% spiral ganglion neurons. To distinguish between them, in situ hybridization for opg RNA was performed (FIG. 3A), combined with immunohistochemistry for TuJ protein and showed that both cochlear neurons and their associated Schwann cells expressed OPG. To test whether OPG was secreted by SGCs, the OPG level in the culture medium was measured by ELISA (FIG. 3B). OPG was abundantly secreted by WT SGCs, even after treating these cells with β-bungarotoxin to eliminate neurons, but was not detected in the culture medium from OPG −/− cells. Although fibroblasts secreted some OPG, the level of secretion was an order of magnitude smaller than that of SGCs (p=0.009).

Figure 3C:
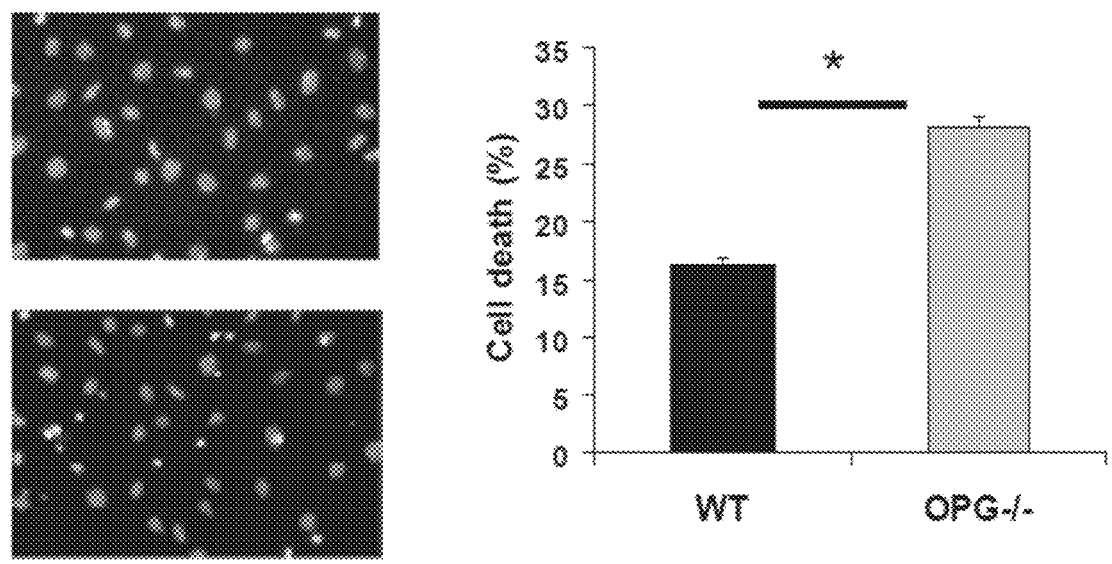

Given that Schwann cells secrete OPG and that they are the first to demonstrate degenerative changes in the opg −/− inner ear, the hypothesis that OPG suppressed apoptosis in cochlear Schwann cells was tested by treating with $H_2O_2$ to produce oxidative stress. Oxidative stress has been shown to cause degeneration of the cochlear nerve after acoustic trauma (Wang Y, Hirose K, Liberman M C. J Assoc Res Otolaryngol. 2002; 3:248-268; van Campen L E, Murphy W J, Franks J R, Mathias P I, Toraason M A. Hear Res. 2002; 64:29-38). Nuclear condensation, a late-stage marker of apoptosis, significantly increased (p=0.003) in opg −/− Schwann cells after $H_2O_2$ treatment compared to that in WT Schwann cells (FIG. 3C).

Figure 4A:
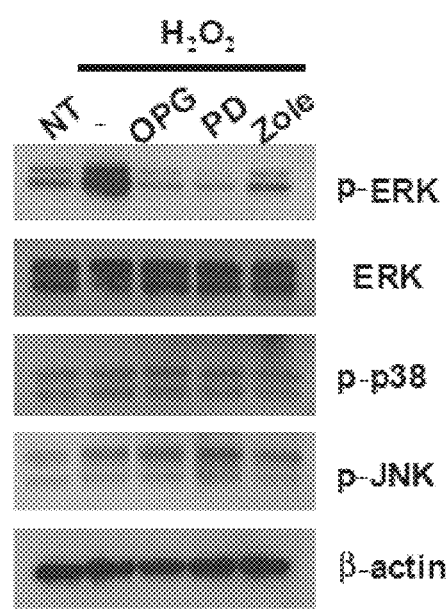
FIG. 4. Sensitization of OPG deficiency cultured Schwann cells to oxidative stress and apoptosis by activating ERK. (A) Treatment of opg –/– Schwann cells with $H_2O_2$ induced ERK kinase activation and had no detectable effect on p38 and JNK. ERK activation was suppressed by pretreatment for 3 hours and co-treatment with either exogenous OPG (100 ng/L), the ERK kinase inhibitor PD 98059 (abbreviated PD, 20 nM), or zoledronate (abbreviated Zole, 10 µM). (B) Exogenous OPG, the ERK inhibitor and zoledronate rescued Schwann cells from death. Pretreatment followed by co-treatment of opg –/– Schwann cells with OPG, PD 98059, or zoledronate rescued $H_2O_2$ induced oxidative cell death. NT: non-treated. N=3. (C) Anti-OPG antibodies suppressed OPG activity, enhanced ERK kinase activity (left), and enhanced cell death (right). N=3.
Figure 4B:
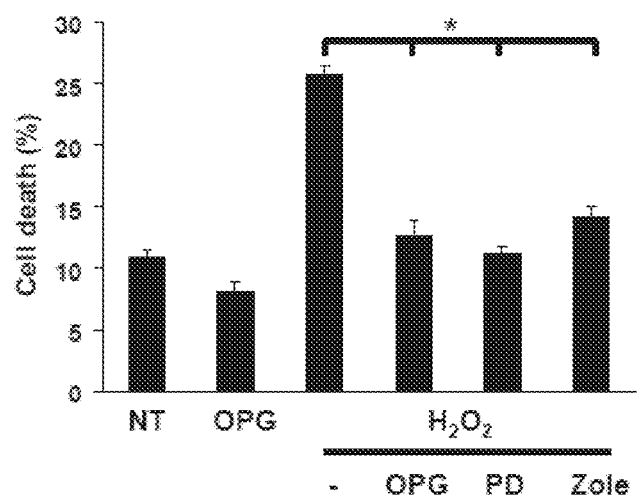
Figure 4C:
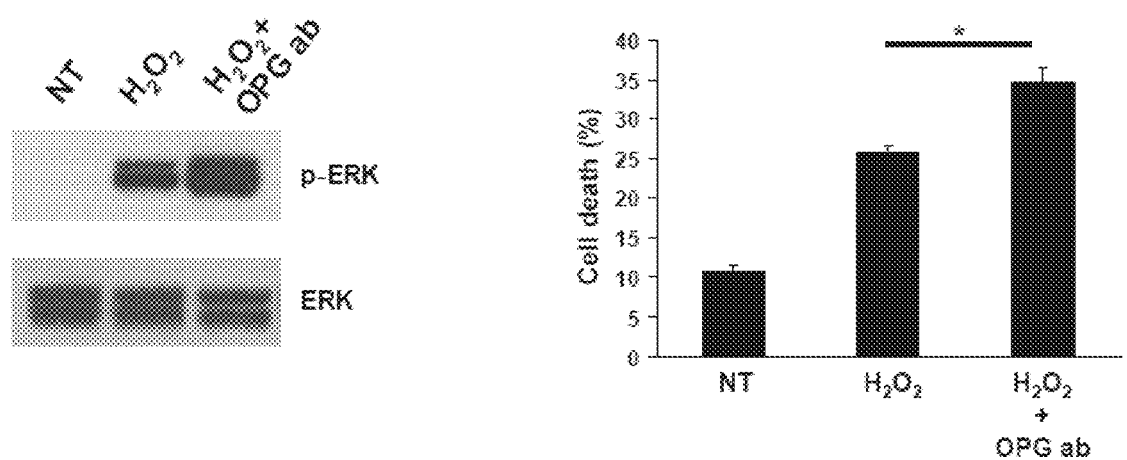

Loss of OPG Expression Sensitizes Cultured Schwann Cells to Apoptosis Induced by Oxidative Stress To investigate the mechanisms that regulate apoptosis caused by the loss of OPG in SGCs, ERK, p38 and JNK signaling pathways were studied because these pathways are known to be regulated by OPG in bone (Khosla S. Endocrinol. 2001; 142:5050-5055) and these pathways have been implicated in hearing loss due to acoustic trauma or ototoxic drugs (Zine A, van de Water TR. Curr Drug Targets CNS Neurol Disord. 2004; 3(4):325-32). After $H_2O_2$ treatment, ERK kinase was activated in WT Schwann cells, as evidenced by the presence of phospho-ERK (p-ERK), but p38 and JNK were not affected (FIG. 4A). This suggested that the activation of ERK signaling induced cell death in SGCs after oxidative stress. The activation of ERK kinase signaling was suppressed by either exogenous OPG, an ERK kinase inhibitor (PD 98059), or zoledronate, a bisphosphonate used to treat osteoporosis and lytic bone lesions due to metastases (Lipton A, et al. Cancer Invest. 2002; 20:s45-s54). Zoledronate was studied because the ERK kinase pathway is a known target of zoledronate in endothelial cells (Hasmim M, Bieler G, Rüegg C. J Thromb Haemost. 2007; 5:166-173). Exogenous OPG, PD 98059, and zoledronate not only suppressed ERK kinase activation but also rescued opg −/− SGCs from oxidative stress induced cell death (FIG. 4B). Without $H_2O_2$ treatment, the exogenous OPG did not significantly affect cell death in opg −/− SGCs (FIG. 4B). Addition of neutralizing OPG antibodies to the culture medium enhanced the $H_2O_2$ induced ERK kinase activation and death in WT SGCs (FIG. 4C), validating that activation of ERK kinase induces apoptosis in SGCs.

OPG Suppresses TRAIL Induced Cell Death

Figure 5A:
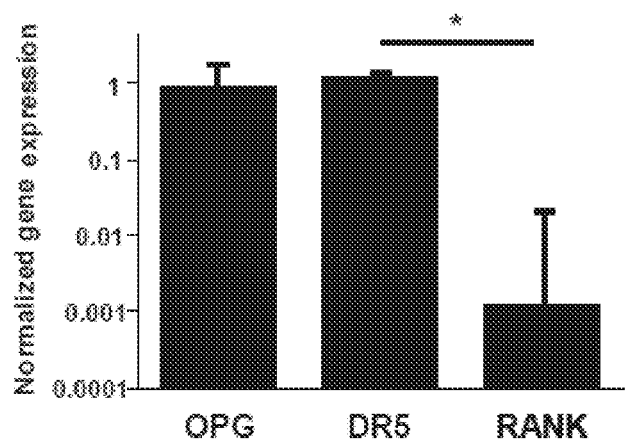
FIG. 5. Suppression of TRAIL induced apoptosis by OPG. (A) Levels of mRNA expression for opg and dr5 were similar, and substantially larger than those for rank in cultured Schwann cells, as determined by real time quantitative RT-PCR. Gene expression levels are normalized to opg expression. N=4. (B) TRAIL induced cell death, as shown by the presence of cleaved caspase 3 and ERK kinase activation (C) in opg –/– Schwann cells. Both cell death (B) and ERK activation (C) was suppressed by exogenous OPG, PD 98059 or zoledronate. TRAIL did not affect p38, JNK or NF-κB p65 activity. Abbreviations were the same as in FIG. 4. Data in (B) and (C) are representative results from 3 independent experiments.
Figure 5B:
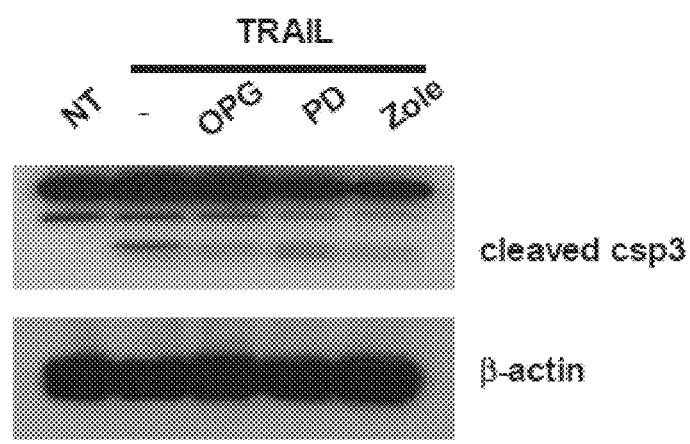

To further probe anti-apoptotic mechanisms of OPG in SGCs, two receptors affected by OPG signaling in other cell types, receptor RANK and death receptor 5 (DR5), were investigated. These receptors have not been previously described in cochlear Schwann cells or neurons. In bone, OPG interacts with RANK ligand (RANKL) to prevent RANKL from binding to RANK, thus inhibiting osteoclast maturation and function (Khosla S. Endocrinol. 2001; 142: 5050-5055). In tumor cells, OPG interacts with TNF-related apoptosis-inducing ligand (TRAIL) to prevent TRAIL from binding DR5, thus inhibiting apoptosis (Emery J G, et al. J Biol Chem. 1998; 273:14363-14367). Both rank and dr5 mRNAs were present in cultured SGCs (FIG. 5A). Treatment of Schwann cells with recombinant TRAIL increased cleavage of caspase 3. The presence of cleaved caspase 3 was suppressed by pretreatment with recombinant OPG, PD98059, or zoledronate (FIG. 5B). These results further confirmed that OPG supports SGCs survival by inhibiting apoptosis mediated by TRAIL.

Figure 5C:
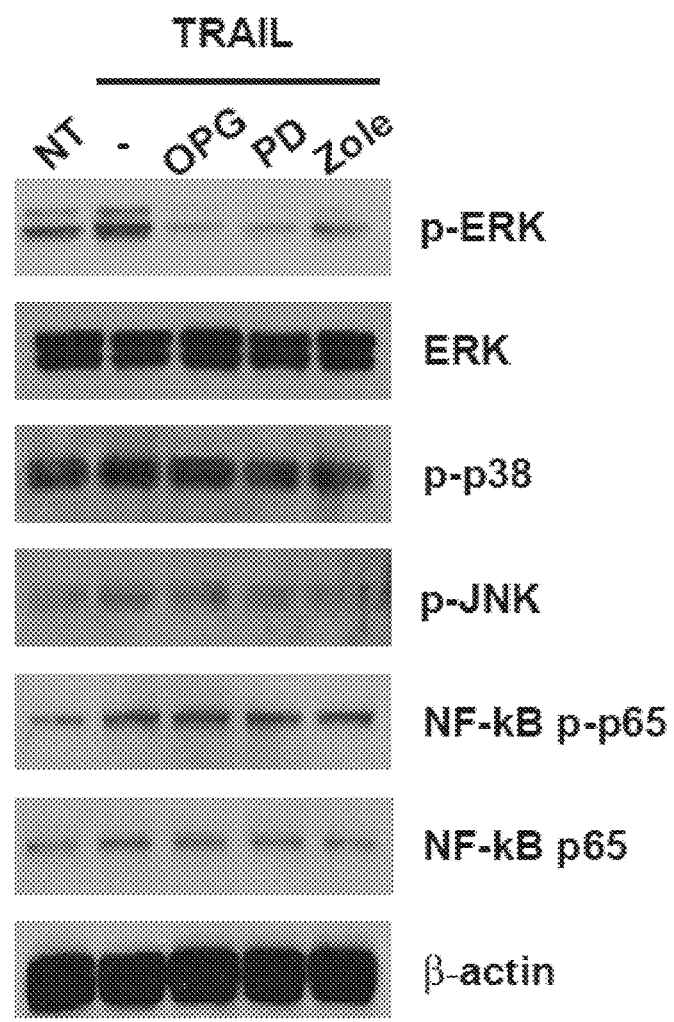

Next, whether OPG suppressed TRAIL induced apoptosis in SGCs by regulating ERK kinase activation was examined. Cells treated with TRAIL activated ERK phosphorylation, which was suppressed by the pretreatment with recombinant OPG, PD98059 or zoledronate (FIG. 5C). These results provide additional evidence that OPG promotes Schwann cells survival via regulation of the ERK kinase pathway.

Figure 6A:
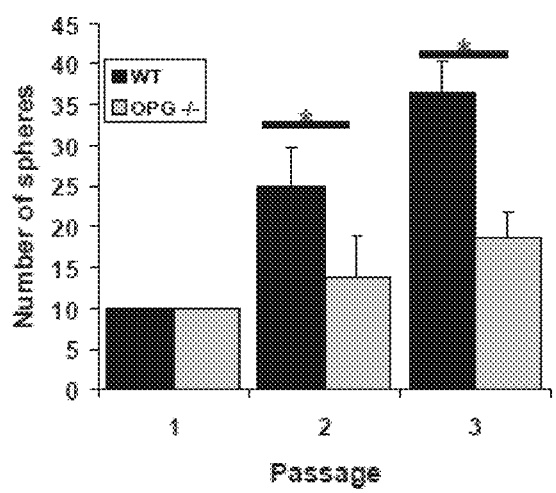
FIG. 6. Reduction of proliferation and survival of floating spheres from the spiral ganglion of the inner ear in opg –/– mice. (A) Ten spheres were picked at the third passage and propagated twice more. The number of WT spheres increased 2-3 times after each passage whereas opg –/– spheres failed to proliferate substantially. (B) Cleaved caspase 3 immunostaining of floating spheres showed increased number of caspase positive cells in opg –/– re WT spheres. (C) When examined with light microscopy, opg –/– spheres were substantially smaller and formed later than WT spheres; the latter were apparent from single cells within 24 hours after passage. Scale bar: 50 µm.
Figure 6B:
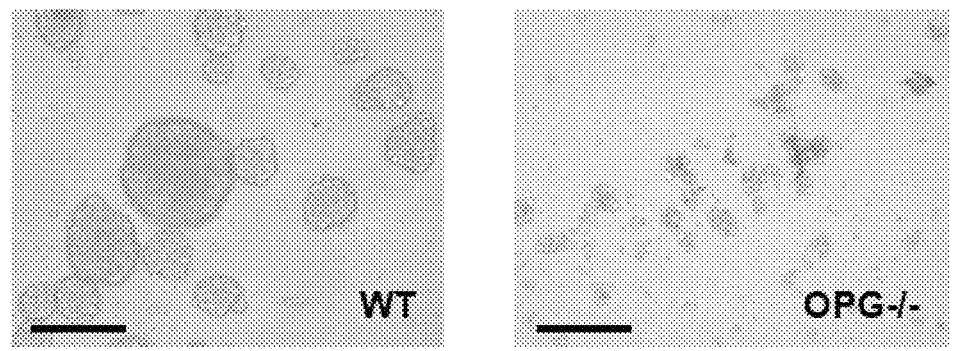
Figure 6C:
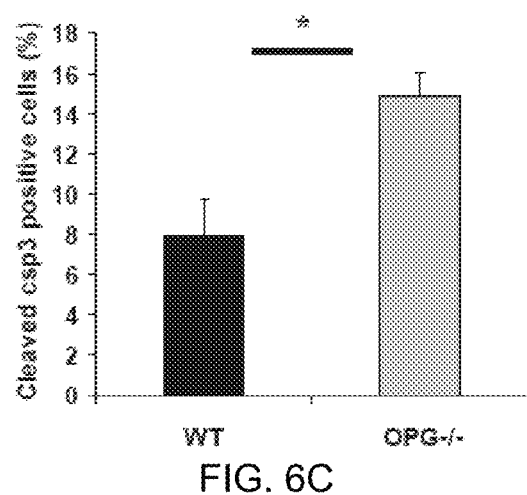

Proliferation Capacity and Morphological Changes in OPG Deficient Auditory Stem Cells Since histological examination of SGCs from opg−/− mouse showed signs of premature aging (FIG. 1C), whether OPG deficiency had an effect on progenitor cells isolated from the SGCs was studied. The ERK pathway, which we have shown to be activated in opg −/− SGCs, is known to influence progenitor cell expansion in the nervous system (Burdon T, Smith A, Savatierc P. Trends Cell Biol. 2002; 12, 432-438). Progenitor cells isolated from the ganglion by sphere formation have the capacity for self-renewal and for differentiation into neurons and glia (Martinez-Monedero R, Yi E, Oshima K, Glowatzki E, Edge A S. Dev Neurobiol. 2008; 68:669-684). WT inner ear progenitor cells abundantly expressed in OPG, RANK and RANKL by real-time RT-PCR, so the effect of OPG deficiency on growth of the spheres was tested. Ten progenitor cells from each group were picked and propagated, and the number of spheres after each passage was counted. Neurospheres from WT mice showed a renewal rate of 2-3 folds after each passage, whereas spheres from OPG −/− mice had a significantly lower rate of self-renewal compared to OPG WT spheres (FIG. 6A). OPG deficiency also affected the size and morphology of neurospheres; while WT spheres were apparent from single cells within 24 hours after passage, sphere formation in OPG−/−mice occurred later, and spheres were generally smaller (FIG. 6B). In addition to slower proliferation rate and smaller morphology, OPG deficiency also resulted in increased death of neurospheres as shown by increased cleaved caspase 3 staining (FIG. 6c) compared to WT spheres.

Figure 7A:
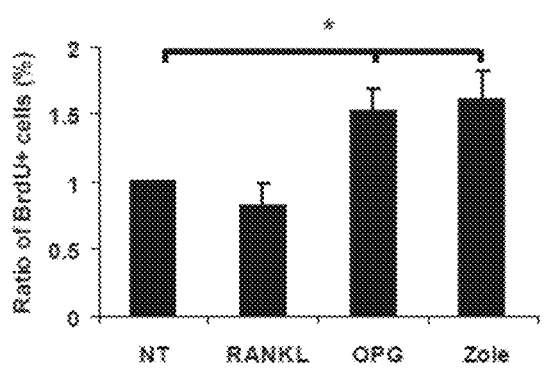
FIG. 7. Promotion of proliferation and suppression of apoptosis in auditory stem cells by OPG. (A) Counting of floating opg –/– spheres treated with BrdU revealed that RANKL treatment reduced, whereas OPG and zoledronate treatment increased the number of BrdU positive cells as demonstrated by the immunocytochemical staining of BrdU. (B) Cleaved caspase 3 staining showed that Rankl treatment increased, whereas OPG and zoledronate treatment decreased the number of caspase positive cells in spheres as demonstrated by the immunocytochemical staining of cleaved caspase 3.
Figure 7B:
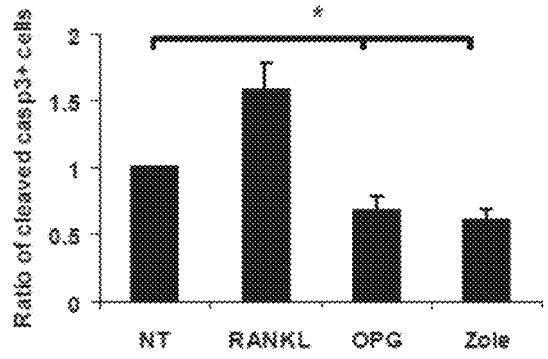

OPG Promotes Proliferation and Suppress Apoptosis in OPG Deficient Auditory Stem Cells Treatment with exogenous OPG or zoledronate significantly enhanced proliferation of opg−/− spheres while the addition of RANKL did not significantly affect the proliferation of opg−/− spheres as shown by the BrdU staining (FIG. 7A). Exogenous OPG or zoledronate not only sustained proliferation, but also suppressed apoptosis in opg−/− spheres. Apoptotic cell death in third generation neurospheres from opg −/− mice and WT control mice was analyzed by staining for cleaved caspase 3. Although treatment of opg −/− spheres with RANKL did not significantly affect proliferation, it significantly increased apoptosis (FIG. 7B). Treatment of opg −/− spheres with OPG and zoledronate reduced apoptotic cell death, indicating that OPG and zoledronate prevented apoptosis in early proliferating neural progenitors of the spiral ganglion cells (FIG. 7B).

REFERENCES

1. Whyte M P. Paget's disease of bone and genetic disorders of RANKL/OPG/RANK/NF-kB signaling. *Ann N Y Acad Sci.* 2006; 1068:143-64.

2. Yasuda H, et al. Osteoclast differentiation factor is a ligand for osteoprotegerin/osteoclastogenesis-inhibitory factor and is identical to TRANCE/RANKL. *Proc Natl Acad Sci USA.* 1998; 95(7):3597-3602.

3. Bucay N, et al. Osteoprotegerin-deficient mice develop early onset osteoporosis and arterial calcification. *Genes Dev.* 1998; 12(9):1260-1268.

4. Kanzaki S, Takada Y, Ogawa K. Matsuo K. Bisphosphonate therapy ameliorates hearing loss in mice lacking osteoprotegerin. *J Bone Miner Res.* 2009; 24:43-49.

5. Qin Z, Wood M, Rosowski J. Measurement of conductive hearing loss in mice. *Hear Res.* 2010; 263:93-103.

6. Hequembourg S, Liberman M C. Spiral ligament pathology: a major aspect of age-related cochlear degeneration in C57BL/6 mice. *J. Assoc. Res. Otolaryngol.* 2001; 2:118-129.

7. Styrkarsdottir U, et al. Multiple genetic loci for bone mineral density and fractures. *N Engl J Med.* 2008; 358(22): 2355-2365.

8. Arko B, Prezelj J, Komel R, Kocijancic A, Hudler P, Marc J. Sequence variations in the osteoprotegerin gene promoter in patients with postmenopausal osteoporosis. J Clin Endocrinol Metab. 2002; 87(9):4080-4084.

9. Brändström H, Stiger F, Lind L, Kahan T, Melhus H, Kindmark A. A single nucleotide polymorphism in the promoter region of the human gene for osteoprotegerin is related to vascular morphology and function. Biochem Biophys Res Commun. 2002; 293(1):13-17.

10. Soufi M, Schoppet M, Sattler A M, Herzum M, Maisch B, Hofbauer L C, Schaefer J R. Osteoprotegerin gene polymorphisms in men with coronary artery disease. J Clin Endocrinol Metab. 2004; 89(8):3764-3768.

11. Yaşil S, Cömlekçi A, Güneri A. Further hearing loss during osteoporosis treatment with etidronate. *Postgrad Med J.* 1998; 74:363-364.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating inner ear sensorineural hearing loss associated with a deficiency in osteoprotegerin (OPG), wherein the hearing loss is associated with degeneration of auditory neurons but not associated with otosclerosis in a subject, the method comprising:
   selecting a subject who has inner ear sensorineural hearing loss associated with a deficiency in OPG and degeneration of auditory neurons but not associated with middle ear otosclerosis; and
   administering to the inner ear of the subject a therapeutically effective amount of an ERK Kinase inhibitor.

2. The method of claim 1, wherein the ERK Kinase inhibitor is a small molecule inhibitor, an antibody or antigen-binding fragment thereof that binds to and inhibits ERK kinase, or an inhibitory nucleic acid that targets ERK kinase.

3. The method of claim 1, wherein the degeneration of auditory neurons is associated with demyelination of auditory neurons.

4. The method of claim 1, wherein the subject has juvenile Paget's disease.

\* \* \* \* \*